(12) United States Patent
Suk et al.

(10) Patent No.: US 10,993,634 B2
(45) Date of Patent: May 4, 2021

(54) IMAGE-GUIDED CLOSED-LOOP ROBOTIC SYSTEM FOR AUTOMATED WHOLE-CELL PATCH CLAMPING ELECTROPHYSIOLOGY OF NEURONS IN VIVO

(71) Applicants: Massachusetts Institute of Technology, Cambridge, MA (US); Georgia Tech Research Corporation, Atlanta, GA (US)

(72) Inventors: Ho-Jun Suk, Cambridge, MA (US); Edward S. Boyden, Cambridge, MA (US); Ingrid van Welie, Newton, MA (US); Brian Douglas Allen, Cambridge, MA (US); Suhasa B. Kodandaramaiah, Minneapolis, MN (US); Craig R. Forest, Atlanta, GA (US)

(73) Assignees: Massachusetts Institute of Technology, Cambridge, MA (US); Georgia Tech Research Corporation, Atlanta, GA (US)

( * ) Notice: Subject to any disclaimer, the term of this patent is extended or adjusted under 35 U.S.C. 154(b) by 725 days.

(21) Appl. No.: 15/643,462

(22) Filed: Jul. 6, 2017

(65) Prior Publication Data
US 2018/0028081 A1 Feb. 1, 2018

Related U.S. Application Data

(60) Provisional application No. 62/359,155, filed on Jul. 6, 2016.

(51) Int. Cl.
*G06K 9/00* (2006.01)
*A61B 5/04* (2006.01)
(Continued)

(52) U.S. Cl.
CPC ........ *A61B 5/04001* (2013.01); *A61B 5/0071* (2013.01); *A61B 5/0538* (2013.01);
(Continued)

(58) Field of Classification Search
None
See application file for complete search history.

(56) References Cited

U.S. PATENT DOCUMENTS 9,498,293 B2  11/2016  Kodandaramaiah et al.
9,668,804 B2   6/2017  Kodandaramaiah et al.
(Continued)

OTHER PUBLICATIONS

Azizian, Mahdi, et al., Computer-Assisted Patch Clamping, 2010 IEEE International Conference on Robotics and Automation, May 3-8, 2010, USA, pp. 4131-4136.
(Continued)

*Primary Examiner* — Atiba O Fitzpatrick
(74) *Attorney, Agent, or Firm* — Norma E. Henderson

(57) ABSTRACT

In an automated methodology for in vivo image-guided cell patch clamping, a cell patch clamping device is moved into position and targeted to a specific cell using automated image-guided techniques. Cell contact is determined by analyzing the temporal series of measured resistance levels at the clamping device as it is moved. The difference between successive resistance levels is compared to a threshold, which must be exceeded before cell contact is assumed. Pneumatic control methods are used to achieve gigaseal formation and cell break-in, leading to whole-cell patch clamp formation. An automated robotic system capable of performing this methodology automatically performs patch clamping in vivo, automatically locating cells through image guidance and by analyzing the temporal sequence of electrode impedance changes. By continuously monitoring the patching process and rapidly executing
(Continued)

actions triggered by specific measurements, the robot can rapidly find target cells in vivo and establish patch-clamp recordings.

20 Claims, 14 Drawing Sheets

(51) Int. Cl.
 *A61B 5/0538* (2021.01)
 *A61B 34/32* (2016.01)
 *A61B 5/00* (2006.01)
(52) U.S. Cl.
 CPC .......... *A61B 5/4064* (2013.01); *A61B 5/6885* (2013.01); *A61B 34/32* (2016.02); *A61B 2503/40* (2013.01)

(56) References Cited

U.S. PATENT DOCUMENTS

| | | |
|---|---|---|
| 2012/0027807 A1 | 2/2012 | Chien et al. |
| 2012/0083861 A1 | 4/2012 | Fried et al. |
| 2016/0184029 A1* | 6/2016 | Peng ................ A61B 34/10 600/424 |
| 2017/0138926 A1* | 5/2017 | Chubykin ........ G01N 33/48728 |

OTHER PUBLICATIONS

Long, B., et al., 3D Image-Guided Automatic Pipette Positioning for Single Cell Experiments in vivo, Scientific Reports, Dec. 22, 2015, 5:18426, USA.

\* cited by examiner

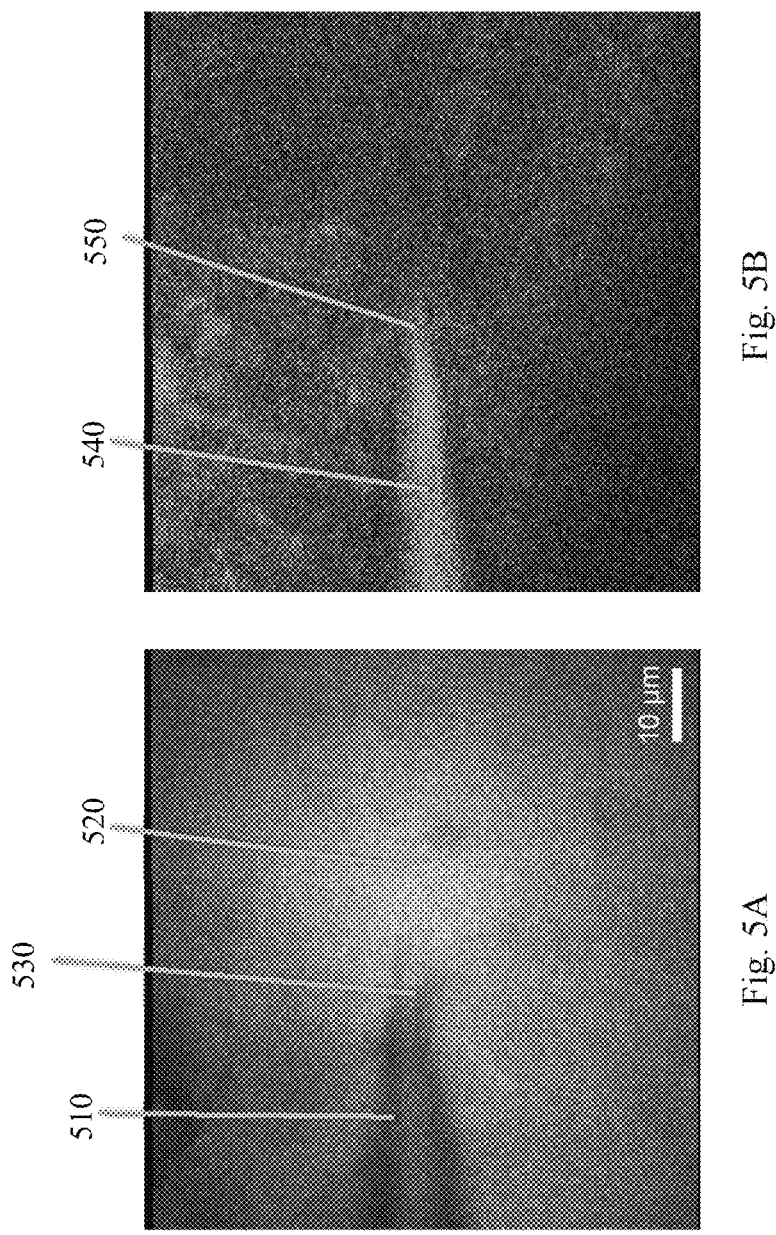

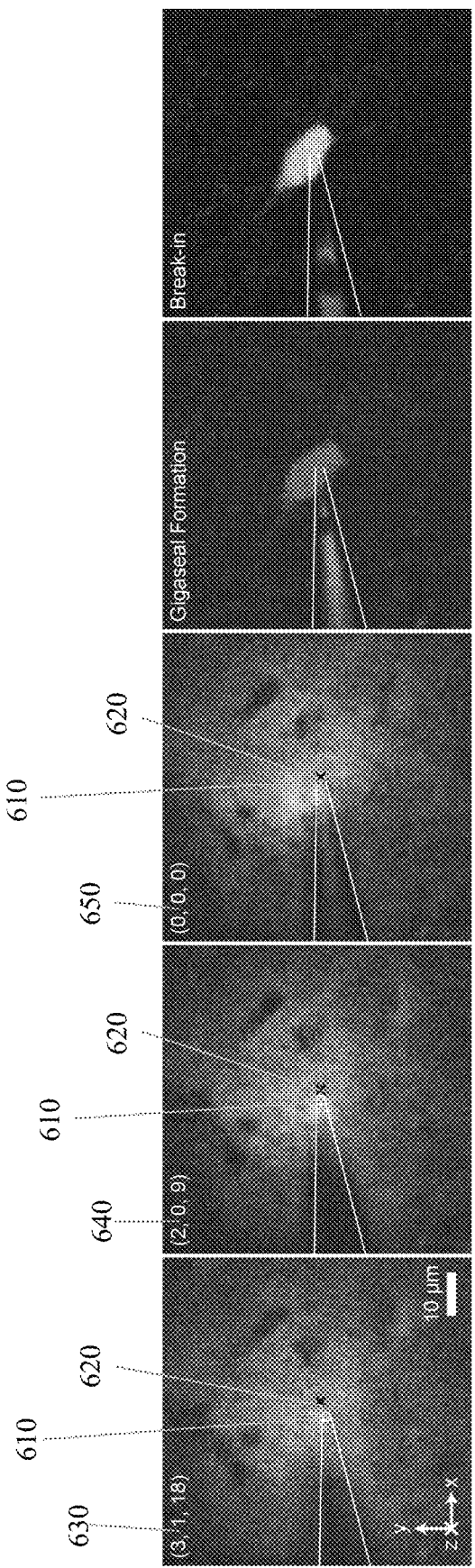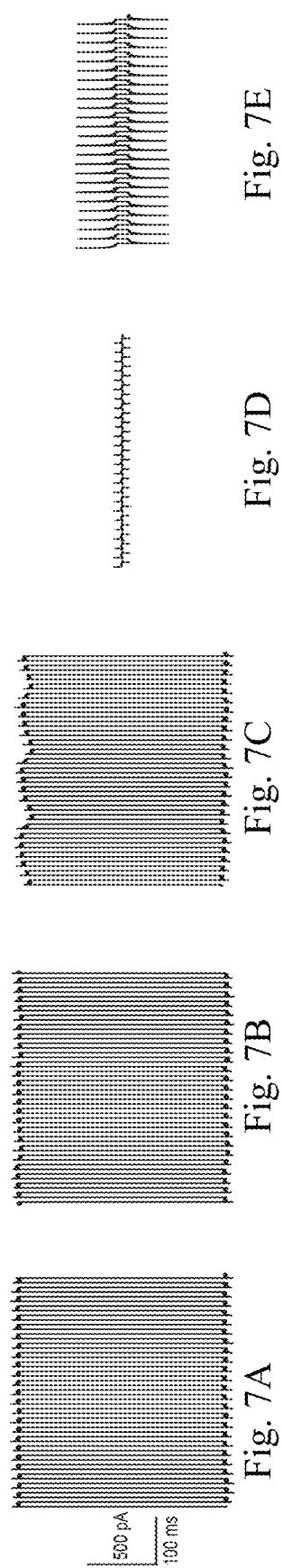

IMAGE-GUIDED CLOSED-LOOP ROBOTIC SYSTEM FOR AUTOMATED WHOLE-CELL PATCH CLAMPING ELECTROPHYSIOLOGY OF NEURONS IN VIVO

RELATED APPLICATIONS

This application claims the benefit of U.S. Provisional Application Ser. No. 62/359,155, filed Jul. 6, 2016.

STATEMENT REGARDING FEDERALLY SPONSORED RESEARCH OR DEVELOPMENT

This invention was made with U.S. Government Support under Grant Number 1R01EY023173, awarded by National Institutes of Health. The Government has certain rights in this invention.

INCORPORATION BY REFERENCE OF MATERIAL SUBMITTED IN COMPUTER-READABLE FORMAT

This application contains a computer program listing appendix submitted in computer-readable format as an electronically-filed text file under the provisions of 37 CFR 1.96 and herein incorporated by reference. The computer program listing appendix text file includes, in ASCII format, the following files: angle_ratio_determination_calibration_HJS.m; distance_to_travel_diff_calc.m; find_cells_gui_SI.m; find_center_and_circle_soma_cell_radius_range.m; find_soma_HJS.m; find_one_pipette_HJS.m; pipette_tip_detection_HJS.m; find_pipette_HJS.m; holding_ voltage_control_HJS.m; image_autopatcher_v1.m; load_sensapex_controller_HJS.m; move_sensapex_manipulator_HJS.m; uman_cleanup_all.m; plot_scalebar_HJS.m; pressure_control_HJS.m; pressure_control_HJS_calibration.m; ramp_pressure_control_HJS.m; ramp_pressure_control_res_meas_HJS.m; and z_stack_acq.m.

FIELD OF THE TECHNOLOGY

The present invention relates to whole-cell patch clamp electrophysiology and, in particular, to a system and method for automated in vivo whole-cell patch clamping.

BACKGROUND

Whole-cell patch clamp electrophysiology of neurons [Hamill, O. P., Marty, A., Neher, E., Sakmann, B. & Sigworth, F. J., "Improved patch-clamp techniques for high-resolution current recording from cells and cell-free membrane patches", Pflugers Arch. Eur. J. Physiol. 391, 85-100 (1981)] has become the "gold standard" for observing electrophysiological properties of individual cells, permitting highly stable, low-noise recordings of neural activities in vivo [Margrie, T. W., Brecht, M. & Sakmann, B., "In vivo, low-resistance, whole-cell recordings from neurons in the anaesthetized and awake mammalian brain", Pflugers Arch. Eur. J. Physiol. 444, 491-498 (2002); Lee, A. K., Epsztein, J. & Brecht, M., "Head-anchored whole-cell recordings in freely moving rats", Nat. Protoc. 4, 385-392 (2009); Lee, A. K., Manns, I. D., Sakmann, B. & Brecht, M., "Whole-Cell Recordings in Freely Moving Rats", Neuron 51, 399-407 (2006]. Whole-cell patch clamp electrophysiology of neurons in vivo enables the recording of electrical events in cells with great precision and supports a wide diversity of morphological and molecular analysis experiments important for the understanding of single-cell and network functions in the intact brain. However, high levels of skill are required in order to perform in vivo patching, and the process is time-consuming and painstaking.

In a typical whole-cell patch clamp electrophysiology implementation, a glass pipette electrode is used to gain electrical and molecular access to the inside of a cell. This permits high-fidelity recording of electrical activity in neurons embedded within intact tissue, such as in brain slices, or in vivo. Whole-cell patch clamp recordings [Hamill, O. P., Marty, A., Neher, E., Sakmann, B. & Sigworth, F. J., "Improved patch-clamp techniques for high-resolution current recording from cells and cell-free membrane patches", Pflugers Arch. 391, 85-100 (1981); Margrie, T. W., Brecht, M. & Sakmann, B., "In vivo, low-resistance, whole-cell recordings from neurons in the anaesthetized and awake mammalian brain", Pflugers Arch. 444, 491-498 (2002)] of the electrical activity of neurons in vivo, which utilize the glass micropipettes to establish electrical and molecular access to the insides of neurons embedded in intact tissue, exhibit signal quality and temporal fidelity sufficient to report synaptic and ion-channel mediated subthreshold events of importance for understanding how neurons compute, and how their physiology can be modulated by brain disorders or pharmaceuticals. In vivo patching of cells in the intact brain presents several capabilities that make it of great use, including that the recordings present extremely high signal-to-noise ratios and thus can be used to reveal subthreshold responses such as synaptic or ion channel events. Current can be delivered into a cell being recorded through a pipette to drive or silence the cell or to support the characterization of specific receptors or channels in the cell.

Whole-cell patch clamping of cells in intact tissue also allows for infusion of chemicals and extraction of cell contents. Molecular access to the cell enables infusion of dyes for morphological visualization, as well as extraction of cell contents for transcriptomic single-cell analysis [Eberwine, J. et al., "Analysis of gene expression in single live neurons", Proc Natl Acad Sci USA 89, 3010-3014 (1992)], thus enabling integrative analysis of molecular, anatomical, and electrophysiological information about single neurons in intact tissue.

However, whole-cell patch clamping of cells in intact tissue is laborious, being something of an art to perform, especially in vivo. Although protocols exist for performing whole-cell patch clamp recording in such conditions, much practice is required by individual investigators to master the technique, since each step in the process of looking for a neuron and establishing the recording requires intuition as well as fast judgment and action. This has limited adoption of this technique in neuroscience to a small number of labs, and also precludes systematic or scalable in vivo patch clamping experiments.

The combination of whole-cell patch clamping with two-photon laser scanning microscopy and fluorescence labeling tools [Margrie, T. W. et al., "Targeted whole-cell recordings in the mammalian brain in vivo", Neuron 39, 911-918 (2003); Komai, S., Denk, W., Osten, P., Brecht, M. & Margrie, T. W., "Two-photon targeted patching (TPTP) in vivo", Nat. Protoc. 1, 647-652 (2006)], called two-photon image-guided patch-clamp, is especially powerful, as it uniquely enables targeted characterizations of specifically identified neurons in the intact brain. However, only a limited number of expert experimenters have been able to utilize this technique to its full potential, because years of training and experience are usually required to learn the intricacies of important procedures and to master all the skills required to perform the technique.

The image-guided automatic pipette positioning system of Long et al. [Long, B., et al., "3D Image-Guided Automatic Pipette Positioning for Single Cell Experiments in vivo", Scientific Reports 5:18426 (2015)] automatically moves a pipette from outside the brain to the position near the target cell and uses two-photon microscope images to correct offsets, but the critical procedures for patch-clamp recordings, such as moving the pipette further to make its tip touch the target cell, forming a tight gigaohm seal by adjusting pressure applied to the pipette, and establishing the whole-cell configuration by applying a strong pulse of suction at the pipette tip, still need to be performed manually.

SUMMARY

Automated two-photon image-guided patch-clamp according to the invention is a powerful technique that uniquely enables specific identification of cells and analysis of their electrophysiological properties in vivo. Building from prior development of an automated "blind", non-image-guided patch system [Kodandaramaiah, S. B. et al., "Assembly and operation of the autopatcher for automated intracellular neural recording in vivo", Nat. Protoc. 11, 634-654 (2016); Kodandaramaiah, S. B., Franzesi, G. T., Chow, B. Y., Boyden, E. S. & Forest, C. R. "Automated whole-cell patch-clamp electrophysiology of neurons in vivo.", Nature Methods 9, 585-587 (2012); U.S. Pat. No. 9,668,804 (2017); U.S. Pat. No. 9,498,293 (2016)], the present invention is, in one aspect, a robotic system that automatically completes the tasks involved in two-photon image-guided patch-clamp recordings. Specifically, a robot according to the invention fully automates movement of a patch pipette onto the targeted cell, formation of a gigaohm seal, and break-in for the whole-cell configuration, all of which are critical for successful patch-clamp recordings.

In one aspect, the invention is an apparatus for automated image-guided cell patch clamping that includes a cell patch formation apparatus that includes at least one cell patch clamping device having a recording electrode pipette, the recording electrode pipette having a tip, a clamping device-positioning 3-axis linear actuator connected to the cell patch clamping device, and a patch amplifier with computer interface. The apparatus also includes a clamping device-moving programmable linear motor connected to the 3-axis linear actuator in a manner permitting moving the cell patch clamping device up and down, an automated imaging system configured for obtaining images of fluorescently-labelled in vivo cells and the recording electrode pipette tip, a resistance monitoring mechanism, and a computer interface configured for automated closed-loop control of the programmable motor based upon a temporal series of resistance measurements at the tip of the recording electrode pipette and on analysis of pipette and target cell images acquired from the imaging system. The apparatus may include controllable pneumatic valves configured for application of pressure and suction to the cell patch clamping device. The pneumatic valves may be configured for applying light suction to the cell patch clamping device during initiation of gigaseal formation and may be configured to apply strong suction to the cell patch clamping device to initiate break-in and whole-cell patch-clamp formation. The automated imaging system may include a two-photon laser scanning microscope.

The apparatus may also include an automated control system configured to cause the tip of the recording electrode pipette to be lowered to a predetermined depth for target cell contact; iteratively causing the tip of the recording electrode pipette to be lowered by a pre-set amount; measuring the resistance at the recording electrode pipette tip after each iteration of the step of lowering; determining whether or not a target cell has been contacted by constructing a temporal series of the resistance measurements after each iteration of the steps of lowering and measuring; after each iteration, imaging the target cell and identifying whether or not the location of the target cell has shifted in the x- or y-direction from the previous target cell location; if the target cell position has shifted, adjusting the recording electrode pipette position in the x- and y-direction to account for the target cell position shift; iteratively continuing the steps until the temporal series of resistance measurements indicates monotonic increases in resistance over a threshold number of consecutive iterations and the increase in resistance over the measured temporal series is above a pre-set detection threshold; stopping the iterative lowering of the recording electrode; initiating gigaseal formation; assessing whether or not gigaseal formation has been achieved; and if gigaseal formation has been achieved, initiating break-in and formation of a whole-cell patch clamp. The automated control system may also be configured for verifying formation of the whole-cell patch clamp, for causing formation of a gigaseal cell-attached patch after gigaseal formation has been achieved and verified, for assessing whether or not the measured resistance has increased over a pre-set tip blockage threshold and, if so, directing the linear motor to retract the cell patch clamping device to indicate tip blockage and failure.

In another aspect, a method for automated image-guided whole-cell patch clamping according to the invention includes the steps of automated imaging of fluorescently-labeled in vivo cells to produce at least one image of potential target cells; identifying and determining the present location of at least one target cell by automated analysis of the at least one potential target cells image; open-loop positioning a pipette tip of an automated cell patch clamping device by causing the tip of the pipette to be lowered to a predetermined depth in preparation for initiation of target cell contact; closed-loop image-guided positioning of the pipette tip to contact the target cell; stopping the closed-loop image-guided positioning of the pipette after target cell contact has been achieved; initiating gigaseal formation; assessing whether or not gigaseal formation has been achieved; and if gigaseal formation has been achieved, initiating break-in and formation of a whole-cell patch clamp. The step of closed-loop image-guided positioning of the pipette tip to contact the target cell includes the steps of determining the initial location of the pipette tip by taking a stack of images around the location of the pipette tip and automatically detecting the initial location of the pipette tip from the stack of images; iteratively lowering the tip of the pipette toward the present location of the target cell by a pre-set amount; measuring the resistance at pipette tip after each iteration of the step of lowering; identifying whether or not a target cell has been contacted by constructing a temporal series of the resistance measurements after each iteration of the steps of lowering and measuring; after each iteration, imaging the target cell and determining whether or not the location of the target cell has shifted in the x- or y-direction from the previous target cell location; if the target cell position has shifted, adjusting the pipette position in the x- and y-direction to account for the target cell position shift; and iteratively continuing the steps until the temporal series of resistance measurements indicates monotonic increases in resistance over a threshold number of consecutive iterations and the increase in resistance over the measured temporal series is above a pre-set target cell detection threshold, indicating target cell contact has been achieved.

The method may further include the steps of verifying formation of the whole-cell patch clamp and forming a gigaseal cell-attached patch after gigaseal formation has been achieved. The step of adjusting the pipette position in the x- and y-direction may include determining x- and y-offsets between the pipette tip and target cell by calculating a current pipette location based on the initial pipette tip location and previous movements of the pipette tip. The step of initiating gigaseal formation may include applying light suction to the cell patch clamping device. The step of initiating break-in and patch clamp formation may include applying strong suction to the cell patch clamping device. The step of determining the initial location of the pipette tip may include identifying the focal plane of the pipette tip by applying filtering and thresholding operations to the images and determining the image in the stack having the brightest pixels most distant from the edge of the image. If a predetermined maximum level for lowering the pipette tip has been reached without target cell contact, or gigaseal formation or break-in has not been achieved, the pipette may be retracted to indicate failure.

In other aspects, the invention includes a method for achieving and verifying target cell contact in an automated image-guided electrophysiology device and a method for controlling an automated image-guided cell patch clamping device.

BRIEF DESCRIPTION OF THE DRAWINGS

Other aspects, advantages and novel features of the invention will become more apparent from the following detailed description of the invention when considered in conjunction with the accompanying drawings wherein:

FIGS. 5A and 5B are example images of a pipette after penetrating through the upper cortical layers of the brain.

FIG. 6A-E is a series of two-photon microscope images showing the automated movement of the pipette to the target cell center to form a gigaseal and to break in, according to one aspect of the present invention.

FIG. 7A-E depicts example raw current traces of the pipette in response to 50 Hz, 10 mV square voltage pulses, with each trace corresponding to a respective image in FIG. 6A-E.

FIGS. 9A-C through FIG. 13 depict example characteristics and recording quality of autopatched cells, wherein:

FIG. 9A-C is a maximum intensity projection (MIP) of a two-photon image stack acquired around an autopatched neuron;

FIG. 13 is a scatter plot of holding current of autopatched neurons as a function of their depth inside the brain.

DETAILED DESCRIPTION

Figure 1:
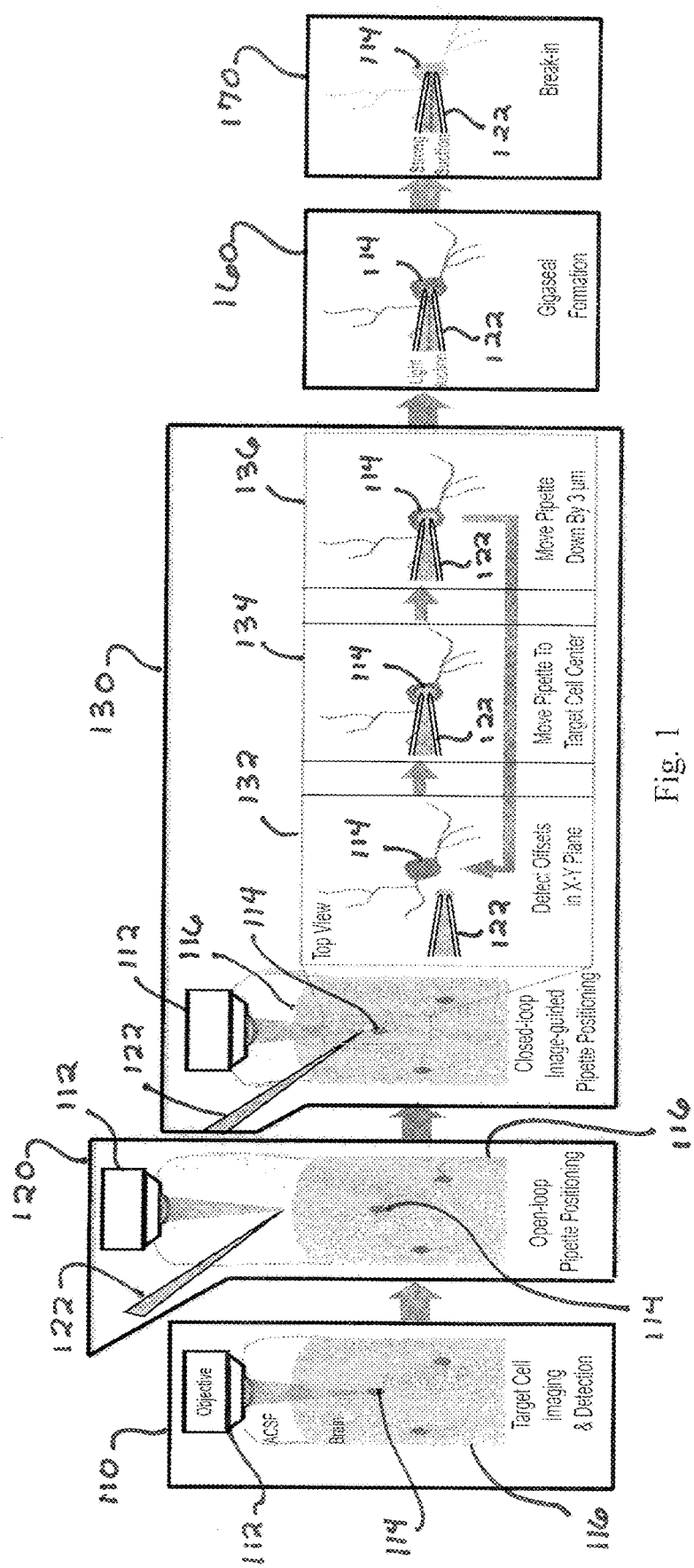
FIG. 1 is a schematic depiction of a preferred embodiment of an automated two-photon image-guided patch clamp methodology for use in an automated two-photon image-guided autopatcher, which is a fully automated system for targeted whole cell recordings in vivo.

In one aspect, the present invention is an apparatus and a methology that enable automated image-guided whole-cell patch clamp recordings in vivo. The invention is related to and builds on the inventions disclosed in U.S. Pat. No. 9,668,804, issued Jun. 6, 2017, which claims the benefit of U.S. Provisional Application Ser. No. 61/558,841, filed Nov. 11, 2011, and U.S. Pat. No. 9,498,293, issued Nov. 22, 2016, which claims the benefit of U.S. Provisional Application Ser. No. 61/726,008, filed Nov. 13, 2012, the entire disclosures of which are herein incorporated by reference.

A robotic system according to the invention automatically completes the tasks involved in two-photon image-guided patch clamp recordings. Specifically, a robot according to the invention fully automates movement of a patch pipette onto the targeted cell, formation of a gigaohm seal, and break-in for the whole-cell configuration, all of which are critical for successful patch-clamp recordings.

With appropriate fluorescence labeling techniques, the current invention can target a specific cell type to record from, making it possible to perform experiments that are not feasible with the previous blind autopatcher. For example, systematic and specific examination of specific target genetically modified cells or sparse cell types can be easily and automatically performed with the current invention, whereas these types of studies are impractical with the blind autopatcher, which is unbiased and tends to capture abundant cell types.

In contrast to the image-guided automatic pipette positioning system of Long et al., the current invention automates the critical procedures for patch-clamp recordings, including moving the pipette further to make its tip touch the target cell, forming a tight gigaohm seal by adjusting pressure applied to the pipette, and establishing the whole-cell configuration by applying a strong pulse of suction at the pipette tip, making it a fully automated system for two-photon image-guided patch clamp recordings.

In one aspect of the invention, closed-loop image-guided pipette positioning inside the brain is a unique feature that allows the system to fully automate patch-clamp recordings. This closed-loop closely mimics the manual approach that an expert experimenter would use to bring a patch pipette onto the target cell membrane, and it can be broken down to three main stages: (i) a target cell image is acquired and its center location is automatically detected to determine if it has moved from its original position due to the movement of the pipette inside the brain; (ii) the x- and y-offsets between the pipette tip and the target cell center are determined based on the pipette location, which is calculated using its initial position and movement, and the pipette is moved to compensate for these offsets; and (iii) the pipette takes a µm-sized step towards the target cell in the z-direction, and the loop returns to the first stage. With this loop, it can be ensured that every target cell movement is accounted for and the pipette tip makes contact with the specific target cell membrane.

FIG. 1 depicts an example embodiment of an automated two-photon image-guided patch clamp methodology for use in an automated two-photon image-guided autopatcher, which is a fully automated system for targeted whole-cell recordings in vivo. In the embodiment of FIG. 1, target cell imaging and detection step 110 employs microscope objective 112 to locate target cell 114 in brain 116. This is followed by open-loop pipette positioning step 120, which positions and prepares pipette 122 for closed-loop image-guided pipette positioning step 130, which comprises the steps of iteratively detecting position offsets 132, moving pipette 122 to target cell 114 center 134, and moving pipette 122 down 136 to contact target cell 114. Once target cell contact is achieved, the steps of gigaseal formation 160, using light suction, and break-in 170, using strong suction, achieve the whole-cell patch clamp.

In a particular aspect, the invention includes a method for automatically detecting the location of the pipette tip from a stack of two-photon images taken around the pipette of interest. The method is developed based on the finding that, for pipettes at a steep angle (for example, from 30 degrees to 60 degrees), the image near or right at the focal plane of the pipette tip has its brightest pixels (i.e. pixels with highest intensity values) further away from the edge of the image compared to the images that are more off-focus. The method applies identical filtering and thresholding operations on all of the images in order to find the brightest pixels and their locations in each image. The image with its brightest locations most distant from the edge of the image is considered at the focal plane of the pipette tip (i.e. the z-location of the image is considered equal to the z-location of the pipette tip).

Figure 2A:
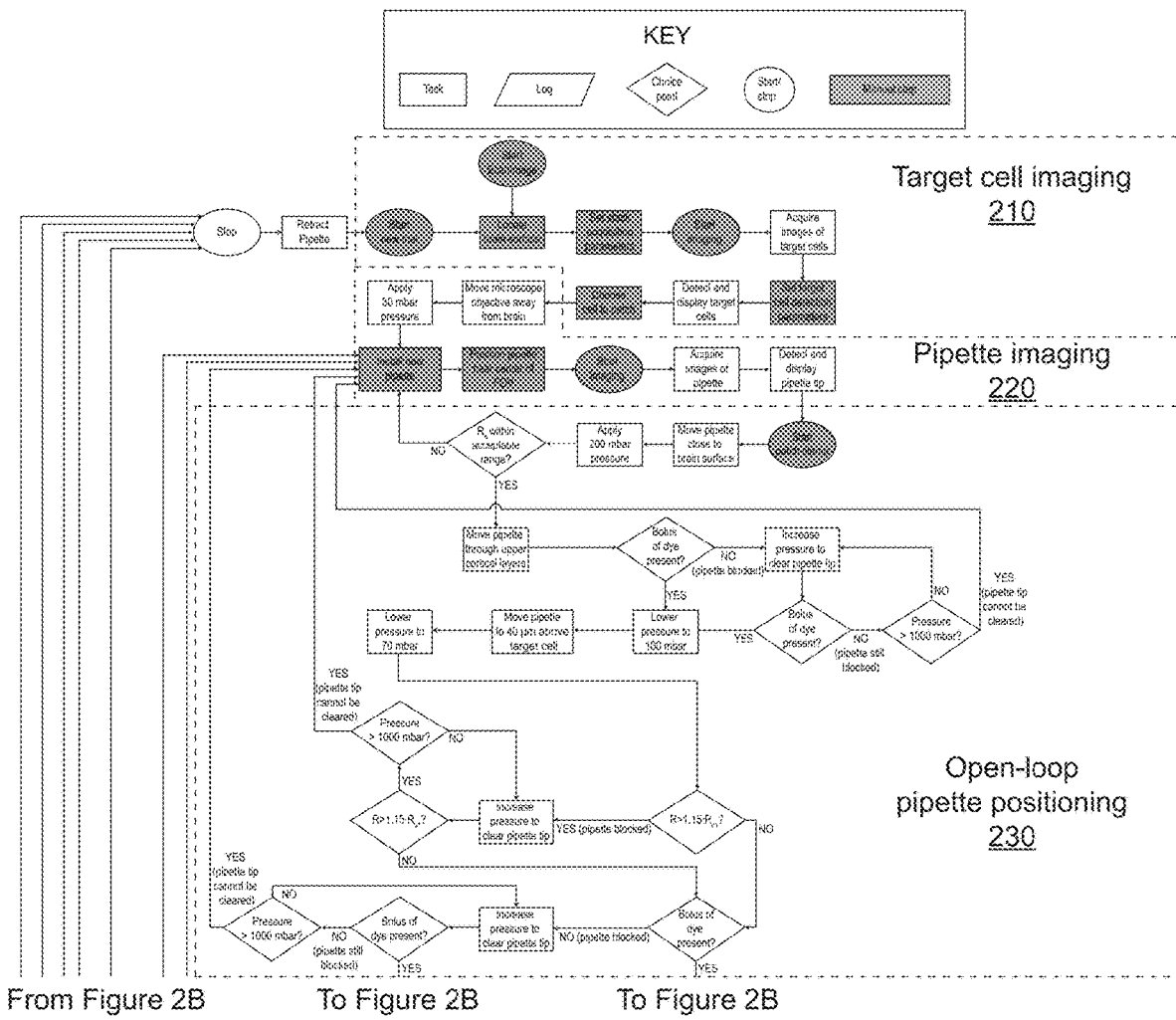
FIG. 2A-C is a flowchart detailing the methodology employed in a two-photon image-guided autopatcher according to the present invention.
Figure 2B:
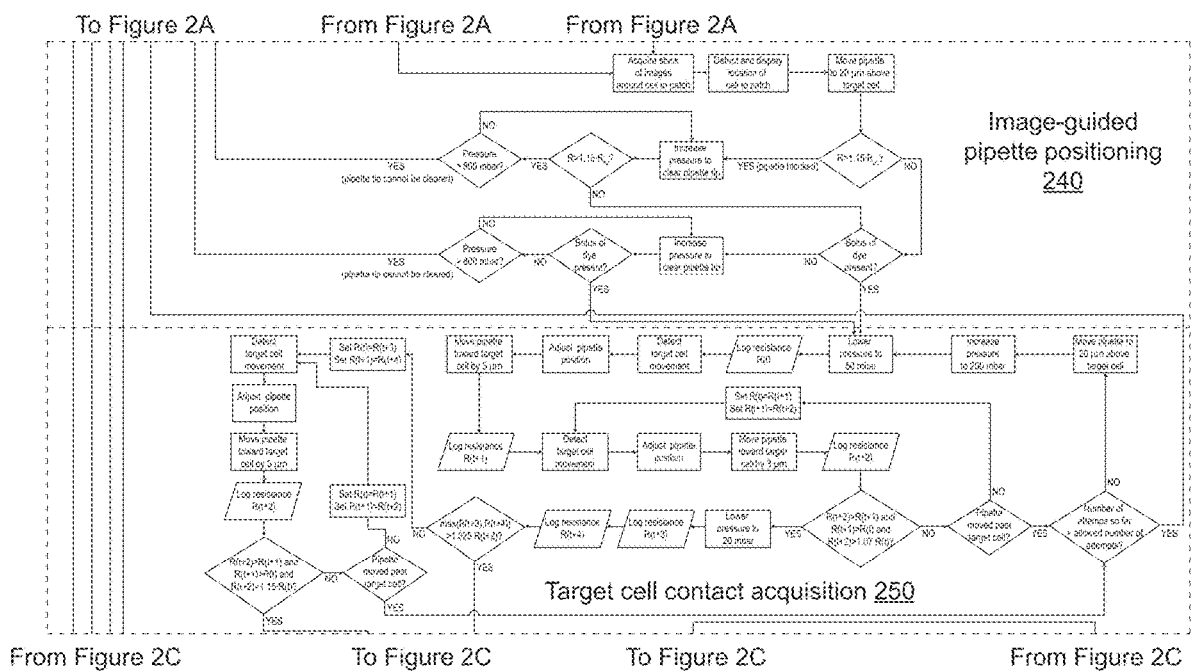
Figure 2C:
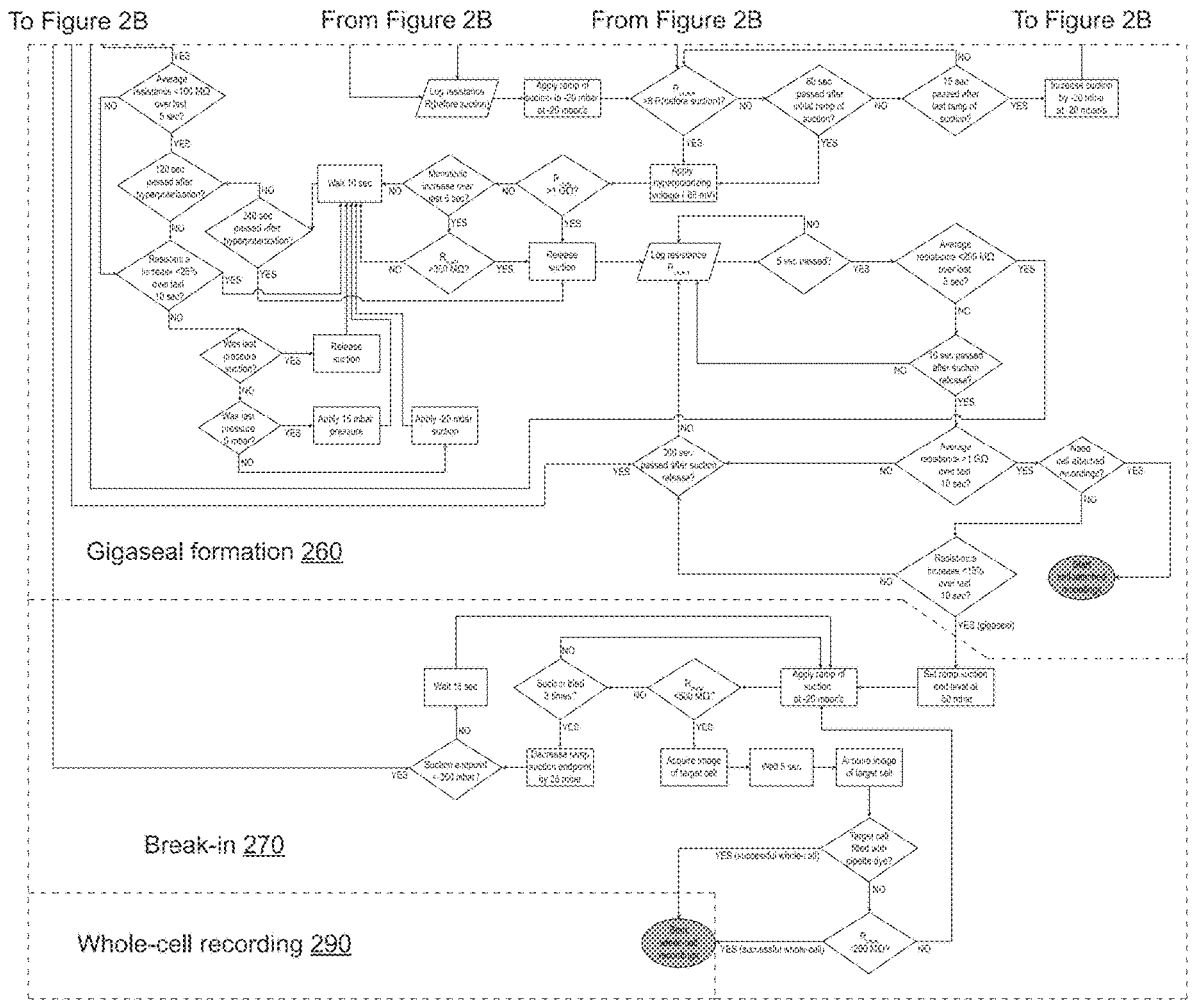

FIG. 2A-C is an overall flowchart of the methodology employed in a preferred embodiment of an automated two-photon image-guided autopatcher, according to the present invention. In FIG. 2A-C, $R_o$ is pipette resistance inside artificial cerebrospinal fluid (ACSF), above the brain surface; $R_{b1}$ is pipette resistance inside the brain, 40 µm above the target cell; $R_{b2}$ is pipette resistance inside the brain, 20 µm above the target cell; R(t) is the first of three consecutive pipette resistance values measured while stepping towards the target cell; R(t+1) is the second of three consecutive pipette resistance values measured while stepping towards the target cell; R(t+2) is the third of three consecutive pipette resistance values measured while stepping towards the target cell; R(t+3) is the first of two consecutive pipette resistance values used to determine if the contact between the pipette and the cell membrane is tight; R(t+4) is the second of two consecutive pipette resistance values used to determine if the contact between the pipette and the cell membrane is tight; R(before suction) is the pipette resistance measured right before suction for sealing is applied; $R_{suction}$ is the pipette resistance measured every 1 second after applying suction during gigaseal formation; $R_{hyper}$ is the pipette resistance measured every 1 second after applying hyperpolarizing voltage during gigaseal formation; $R_{sealing}$ is the pipette resistance measured every 1 second after releasing suction during gigaseal formation; and $R_{break}$ is the pipette resistance measured every 1 second during break-in.

Figure 3:
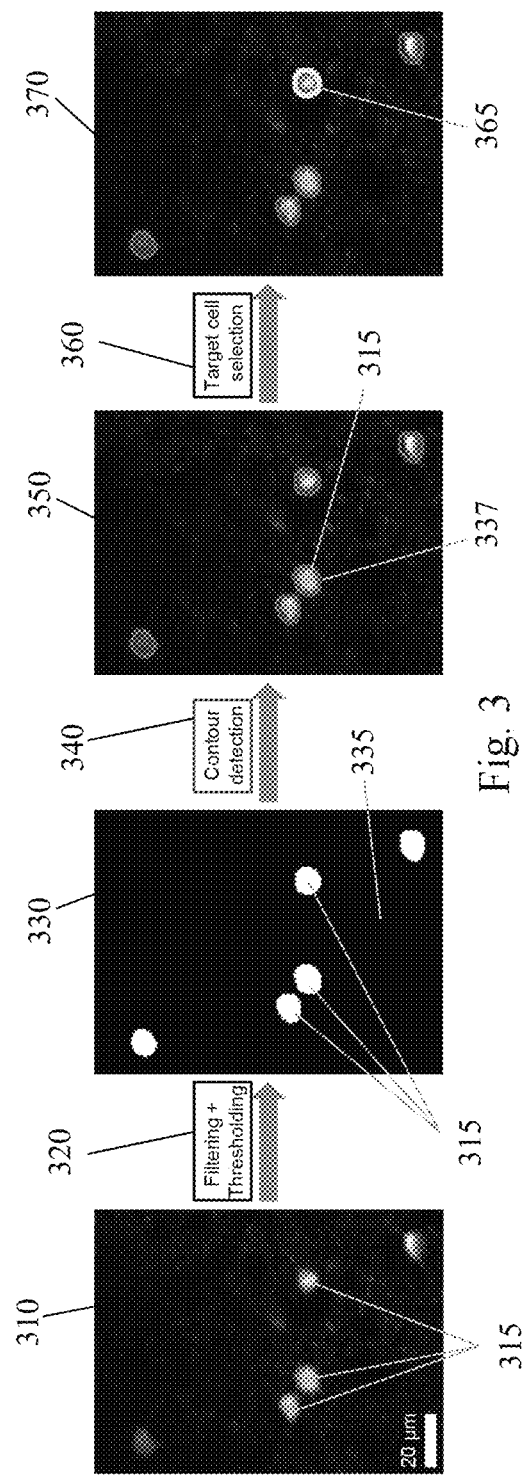
FIG. 3 depicts a cell detection and selection method, according to one aspect of the present invention.

As shown in FIG. 2A, during target cell imaging stage 210, the system performs automated imaging and identification of fluorescently-labeled cells inside the brain, after which a target cell to patch is selected (FIG. 3). This is followed by pipette imaging stage 220, during which a pipette is installed, initial pipette images are acquired, and the initial location of the pipette tip is identified. The patch clamp process is initiated by open-loop pipette positioning stage 230, during which the pipette is prepared for clamping and moved into an initial location above the target cell.

As shown in FIG. 2B, during closed-loop image-guided pipette positioning stage 240, the robot performs image-guided lowering of the pipette to the appropriate depth for the step of target cell contact acquisition 250. During target cell contact acquisition stage 250, the robot iteratively moves the pipette and measures the resistance in order to determine whether or not the target cell has been contacted. If, as determined by the resistance measurements, the target cell has not been successfully contacted after the pipette distance has been repeatedly adjusted and the maximum probe depth has been reached, the pipette is retracted back to the surface for possible installation of a new pipette. If, as determined by the resistance measurements, the target cell has successfully been contacted, gigaseal formation stage 260 begins (FIG. 2C).

As shown in FIG. 2C, during gigaseal formation stage 260, the robot applies suction pulse and hyperpolarizing voltage to achieve a gigaseal. Once gigaseal formation 260 is achieved and verified, break-in stage 270 begins. During break-in stage 270, break-in is initiated by application of a suction pulse, leading hopefully to a successful whole cell patch clamp. Alternatively, or in addition, a gigaseal cell-attached patch may be achieved. Once a successful whole-cell patch clamp is achieved, whole-cell recording 290 may begin.

An aspect of the autopatcher automated methodology is that the robot analyzes the temporal series of the measured pipette resistances in order to determine whether a cell has been located or not. In the preferred embodiment, the robot computes the difference between successive pipette resistances and compares it to a constant threshold. This can be expressed as:

For a series of multiple consecutive pipette positions (equal or unequal in spacing), 1 to n, with r(n) being the measurement of the resistance at position n and n is greater than or equal to 2, a neuron that is suitable for patching has been encountered if:

$$r(n)-r1 > \text{threshold, where } n > 1$$

$$r(n) > r(n-1)$$

For example, a neuron suitable for patching has been encountered at position 3, if r3−r1>threshold and r3>r2>r1. It will be clear to one of skill in the art that the execution of this algorithm would be extremely difficult, if not impossible, for humans to perform manually in a rapid, systematic way. The systematic execution of such a series of steps in time (i.e., monitoring resistance, determining position, voltage, and pressure) has therefore not before been possible. Automated in vivo cell patching according to the invention works because the algorithm employed overcomes this problem and also mitigates the challenges of the noisy environment, such as heart beat, breathing, and non-neuronal cells.

A preferred embodiment of the method starts with automated imaging and identification of fluorescently-labeled cells inside the brain, after which the user can select a target cell to patch. FIG. 3 depicts a preferred embodiment of a cell detection and selection method, according to one aspect of the present invention. In FIG. 3, raw image 310 of fluorescently labeled cells 315 is filtered and thresholded 320 to isolate 330 the cells 315 from the background 335. The contour 337 of each cell 315 is then traced and overlaid 340 on the original raw image to produce contour image 350. Finally, a cell is selected 360 to patch, the boundary of which 365 is shown highlighted 370.

The microscope objective is then moved away from the brain, providing enough space for the user to install a fluorescent dye-filled patch pipette into the pipette holder and to bring it into the field-of-view inside the artificial cerebrospinal fluid (ACSF) above the brain. Following this open-loop pipette positioning, the pipette tip is automatically detected (FIG. 4), and its location is used to calculate the optimal trajectory to the target cell. Before moving along this trajectory, high positive pressure (for example, but not restricted to, 150-200 mbar) is applied to the pipette, and the pipette resistance inside the ACSF is recorded.

Figure 4:
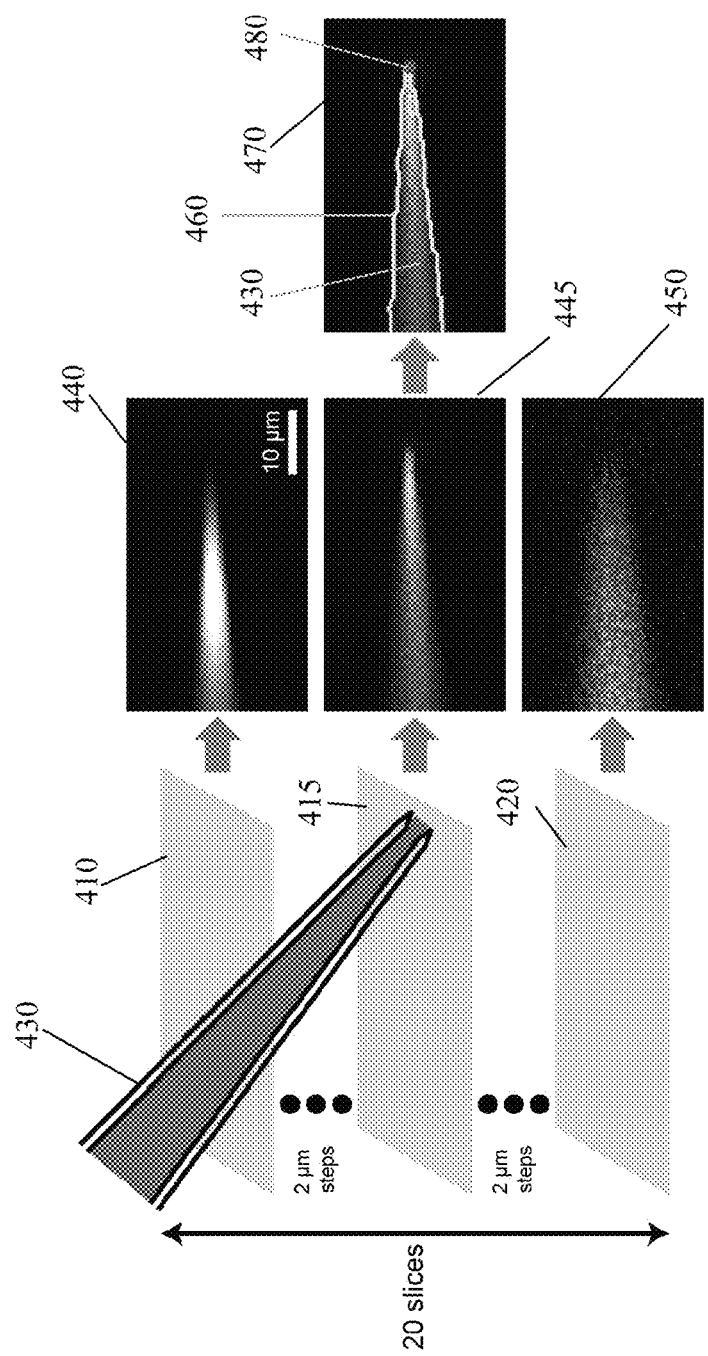
FIG. 4 is a schematic representation of pipette tip detection, according to one aspect of the present invention.

FIG. 4 is a schematic representation of pipette tip detection. In FIG. 4, 20 image slices, represented by the three example slices 410, 415, 420 shown, each separated by a 2 μm step, are acquired around fluorescent dye-filled pipette 430. Each slice captures shapes and characteristics that are unique to the specific z-location from which the image is acquired. For the three example slices: slice 410, image 440 acquired 20 μm above pipette tip 430; slice 415, image 445 acquired at pipette tip 430; slice 420, image 450 acquired 20 μm below pipette tip 430. From these slices, the closest slice to the pipette tip is determined in order to calculate the z-location of the tip, and the pipette boundary within this image is traced 460 to detect 470 the x-y location of the tip 480

Once the pipette is positioned in the upper cortical layers, its resistance is measured again to check if any significant increase (for example, but not limited to, by 15%) has occurred while penetrating the brain surface, using this change as an indication of pipette contamination or blockage. Another indication of pipette blockage is the presence of fluorescent dye around the pipette tip (FIGS. 5A-B), which the method checks for in a preferred embodiment. In case of a significant resistance increase, or little to no dye flowing out of the pipette tip, this embodiment of the method attempts clearing the pipette tip by applying a brief pulse of high positive pressure. However, if the original resistance cannot be recovered or dye cannot be ejected from the pipette tip even after several pulses, the contaminated pipette is retracted automatically to be replaced with a new pipette.

FIGS. 5A and 5B are example images of a pipette after penetrating through the upper cortical layers of the brain. Shown in FIG. 5A is clean pipette 510 ejecting fluorescent dye 520 around its tip 530. Shown in FIG. 5B is a contaminated pipette 540 with no dye being ejected from the tip 550 even with high positive pressure.

In one embodiment, if the pipette tip is clean, it is initially moved to the position 50 μm above the original center position of the target cell, and a new image stack is acquired around the target cell to detect any movement of the target cell due to the insertion of the pipette into the brain. With the updated target cell position, the pipette is then moved to the position 25 μm above the target cell center, and the method enters the closed-loop pipette positioning stage. The closed-loop starts by re-capturing an image of the target cell and detecting its movement. Next, the pipette moves in the x- and y-directions to compensate for the offset between the pipette tip and the target cell center. This pipette position adjustment in the x-y plane is followed by a 3 μm step towards the cell in the z-direction, and the method returns to the start of the loop, where another image is acquired to determine the new offset.

The method remains in this loop until the pipette tip makes contact with the target cell membrane, which is indicated by both visual (pipette tip within the boundary of the target cell soma; FIGS. 6A-C) and electrical (pipette resistance increase that exceeds a certain threshold; FIGS. 7A-C) signals.

FIGS. 6A-E and FIGS. 7A-E depict example two-photon microscope images and raw current traces, respectively, each image and trace corresponding to the closed-loop image-guided pipette positioning stage, the gigaseal formation stage, or the break-in stage. In FIG. 6A-E, a series of two-photon microscope images show the automated movement of the pipette to the target cell center (FIG. 6A-C), to form a gigaseal (FIG. 6D), and to break in (FIG. 6E). The circle 610 marks the pipette tip location, the cross 620 marks the target cell center, and (x, y, z) 630, 640, 650 are the offset from the pipette tip to the target cell center in Cartesian coordinates, moving to (0, 0, 0) by FIG. 6C. In FIG. 7A-E, example raw current traces of the pipette in response to 50 Hz, 10 mV square voltage pulses are depicted, with each trace in FIG. 7A-E corresponding to the associated image in FIG. 6A-E.

As shown in previous studies describing the manual two-photon image-guided patch clamp process [Margrie, T. W. et al., "Targeted whole-cell recordings in the mammalian brain in vivo", Neuron 39, 911-918 (2003); Komai, S., Denk, W., Osten, P., Brecht, M. & Margrie, T. W, "Two-photon targeted patching (TPTP) in vivo", Nat. Protoc. 1, 647-652 (2006); Musser, M. & Margrie, T. W., "Two-photon targeted patching and electroporation in vivo", Cold Spring Harb. Protoc. 2014, 78-85 (2014)], a clear heartbeat modulation of the pipette current was observed when the cell membrane was hit by the pipette tip (FIG. 7C). In some embodiments, this observation may be used in the method to complement or replace the resistance change as the signal for pipette-cell membrane contact.

The next stage, gigaseal formation, is implemented by dynamically applying light suction and hyperpolarization voltage. When a stable gigaohm seal is established, the method moves to the break-in stage, in which a ramp of strong suction is applied to rupture the patch of membrane and achieve the whole-cell configuration.

A robotic system capable of executing this method integrates the previously developed autopatcher control box [Kodandaramaiah, S. B., Franzesi, G. T., Chow, B. Y., Boyden, E. S. & Forest, C. R., "Automated whole-cell patch-clamp electrophysiology of neurons in vivo", Nature Methods 9, 585-587 (2012); Kodandaramaiah, S. B. et al., "Assembly and operation of the autopatcher for automated intracellular neural recording in vivo", Nat. Protoc. 11, 634-654 (2016)] with automated control of a two-photon image-guided patch-clamp rig. The autopatcher system is described in detail in U.S. patent application Ser. No. 13/676,082, filed Nov. 13, 2012, now U.S. Pat. No. 9,668, 804 (2017), and U.S. patent application Ser. No. 14/079,630, filed Nov. 13, 2013, now U.S. Pat. No. 9,498,293 (2016), which are herein incorporated by reference in their entireties.

Figure 8:
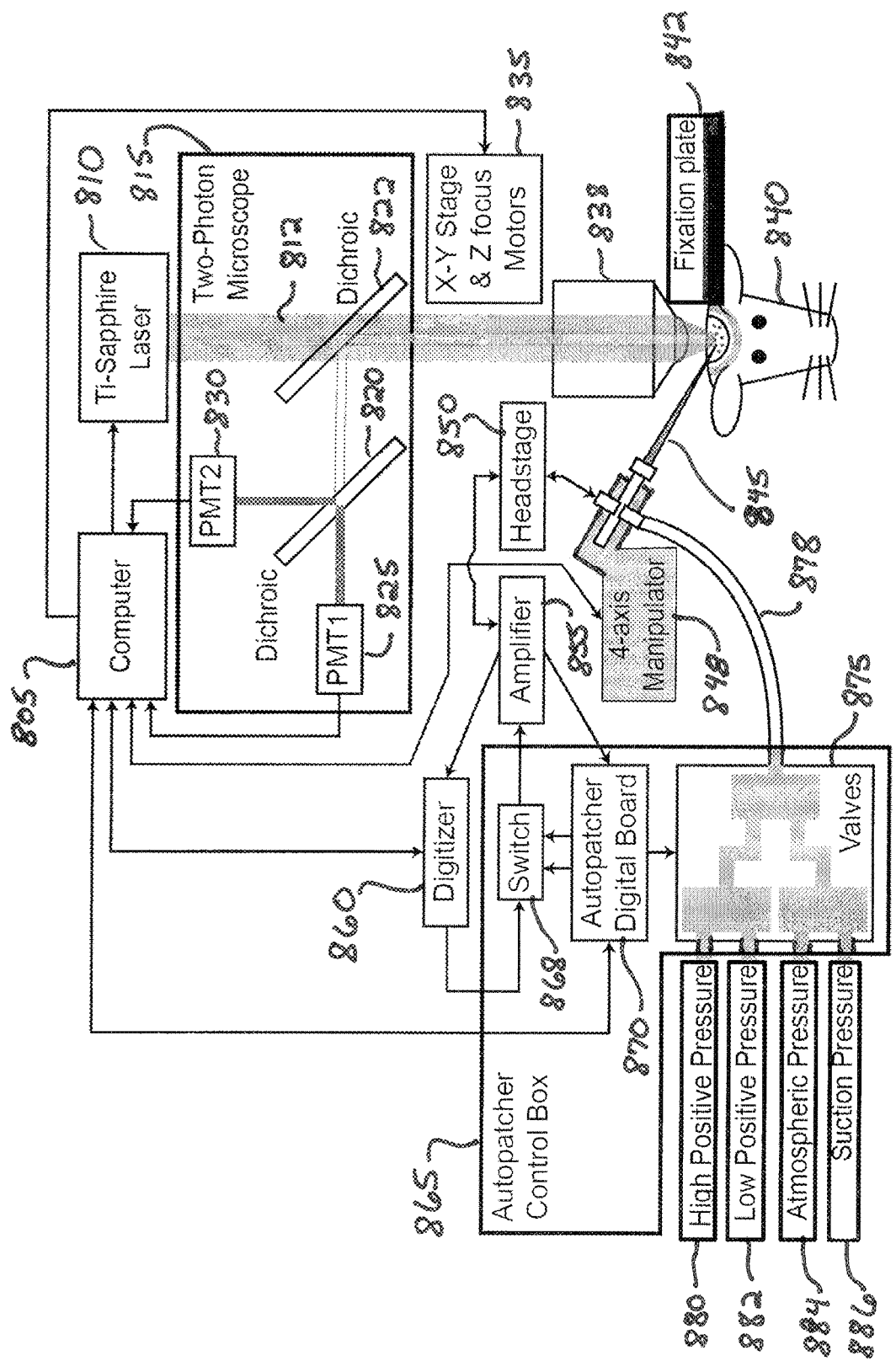
FIG. 8 is a schematic representation of an example two-photon image-guided autopatcher, which integrates a blind autopatcher with a two-photon laser scanning microscope, according to one aspect of the invention.

FIG. 8 is a schematic representation of a two-photon image-guided autopatcher, which integrates the previously developed "blind" autopatcher with a two-photon laser scanning microscope. Shown in FIG. 8 are control computer 805, which controls laser 810 that produces light 812 for two-photon microscope 815. Two-photon microscope 815 comprises dichroics 820, 822, PMT1 825, and PMT2 830. Computer 805 also controls x-y stage and z-focus motors 835. Objective 838 is shown above test subject 840, which is held in place by fixation plate 842. Pipette 845 is held and positioned by 4-axis manipulator 848 and headstage 850. Amplifier 855 communicates with digitizer 860 and autopatcher control box 865, which comprises switch 868, autopatcher digital board 870- and valves 875. Valves 875 provide pressure to pipette 845 via tubing 878, with possible values of high positive pressure 880, low positive pressure 882, atmospheric pressure 884, and suction pressure 886.

In order to implement the invention, it was necessary to develop both a means for automated control of the image acquisition system and a means for analyzing and utilizing the data acquired from the image acquisition system to control the "blind" autopatcher. For automated image acquisition and analysis, in a prototype embodiment, the two-photon microscope and stage motors are controlled by a MATLAB-based module that runs in parallel with ScanImage [Pologruto, T. A., Sabatini, B. L. & Svoboda, K., "ScanImage: flexible software for operating laser scanning microscopes", Biomed. Eng. Online 2, 13 (2003)], an open-source software package commonly used for in vivo image-guided patch-clamp recordings. The module also communicates with a micromanipulator and the autopatcher control box to automate pipette movement onto the target cell, gigaseal formation, and break-in. When tested on tdTomato-labeled parvalbumin (PV)-positive interneurons in the mouse cortex, the system could achieve the whole-cell configuration in 9±4 minutes from the time a patch pipette is placed inside the ACSF above the surface of the brain.

Figures 9A, 9B, 9C:
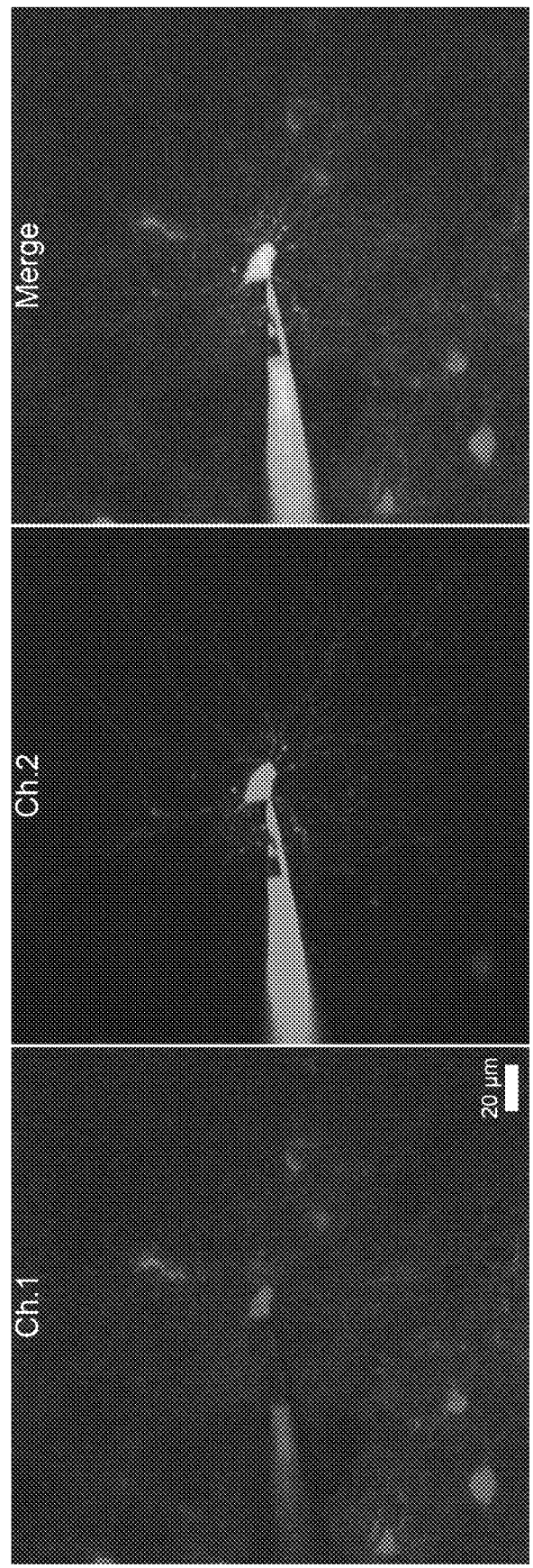
Figure 10:
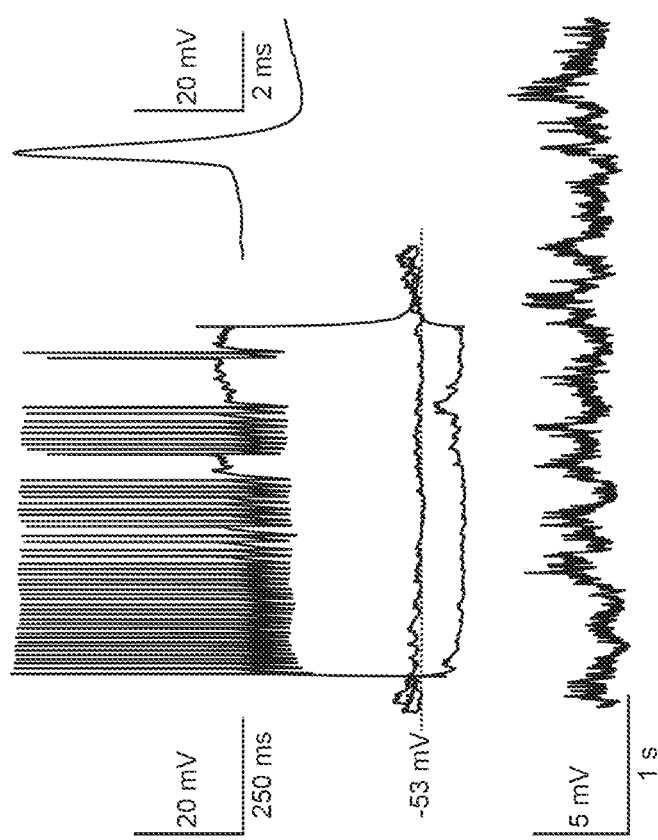
FIG. 10 depicts voltage recordings from an autopatched neuron under current-clamp, with 0.75-second long current injections (−70, 0, and 350 pA; top) and at rest (bottom)

FIGS. 9A-C through FIG. 13 depict example characteristics and recording quality of autopatched cells achieved using the prototype embodiment. A maximum intensity projection (MIP) of a two-photon image stack acquired around an autopatched cell and its voltage traces under current clamp are shown in FIGS. 9A-C and FIG. 10, respectively. Shown in FIG. 9A-B are the separate image channels, with FIG. 9C depicting the merged image. Shown in FIG. 10 are voltage recordings from an autopatched neuron under current-clamp, with 0.75-second long current injections (−70, 0, and 350 pA; top) and at rest (bottom).

Figure 11:
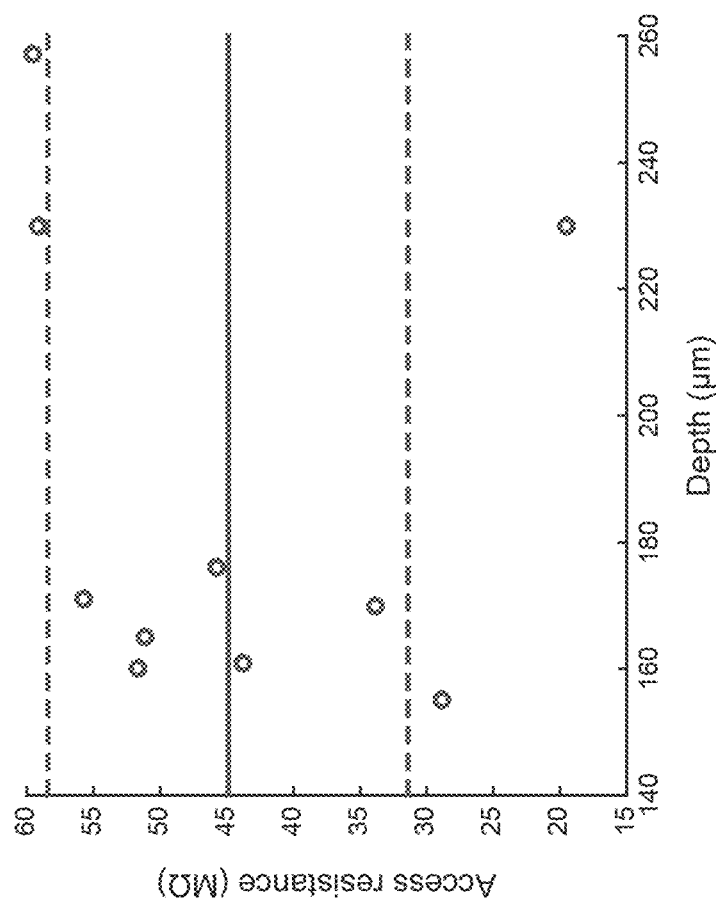
FIG. 11 is a scatter plot of access resistance of autopatched neurons as a function of their depth inside the brain.
Figure 12:
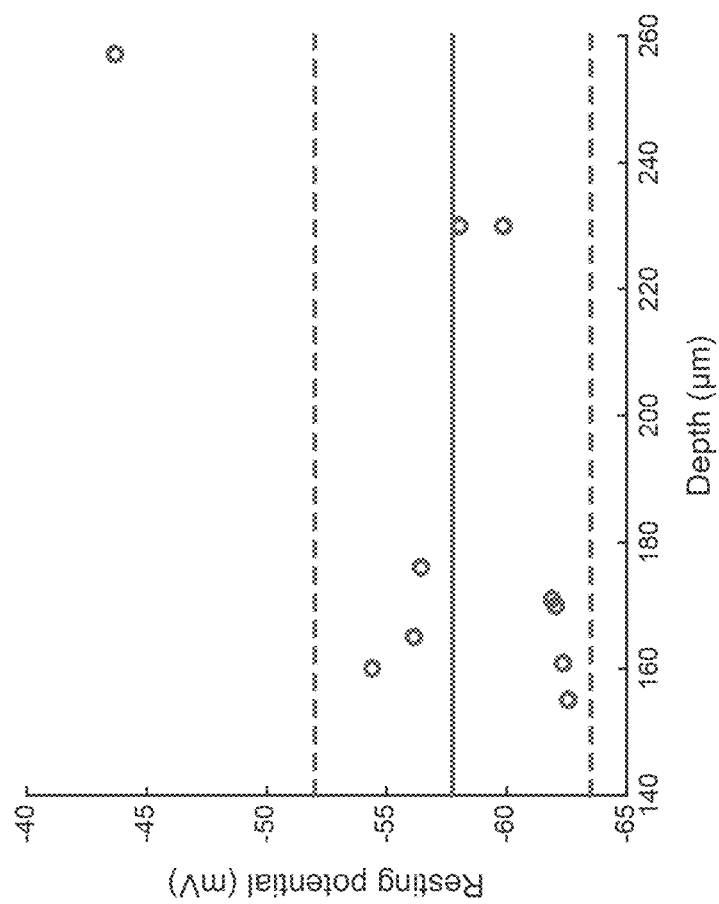
FIG. 12 is a scatter plot of resting potential of autopatched neurons as a function of their depth inside the brain.
Figure 13:
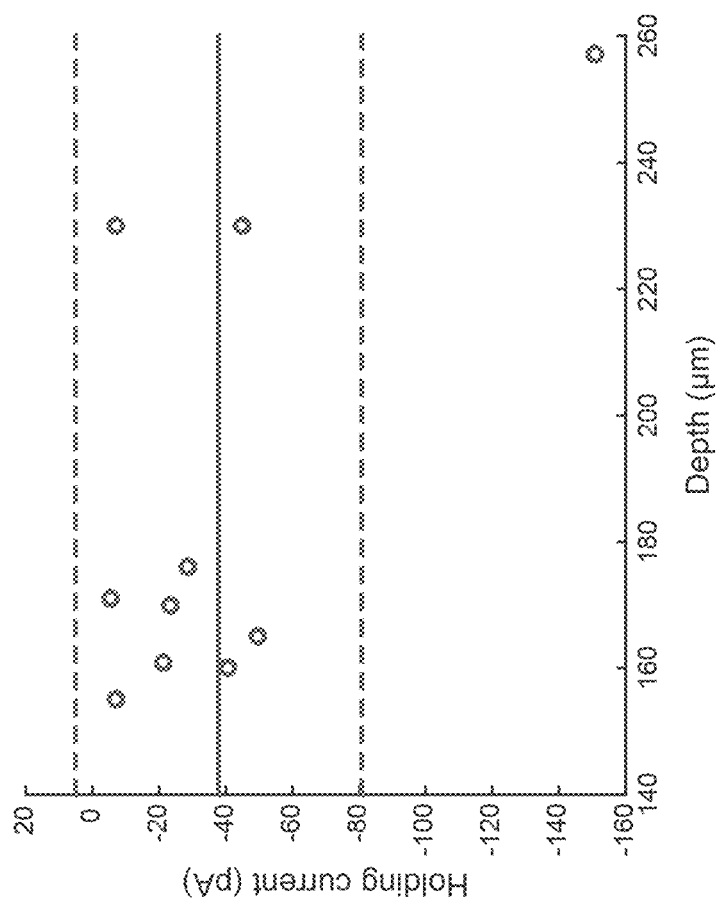

Metrics of recording quality of PV-positive interneurons patched by the system (n=10), such as access resistance, resting potential, and holding current (FIGS. 11-13), were not significantly different when compared to those of the same cells patched fully manually in acute brain slices or in vivo (n=5; Student's t-test with 95% confidence level; P=0.1024 for access resistance; P=0.9755 for resting potential; P=0.4960 for holding current). FIG. 11 is a scatter plot of access resistance of autopatched neurons as a function of their depth inside the brain; FIG. 12 is a scatter plot of resting potential of autopatched neurons as a function of their depth inside the brain; and FIG. 13 is a scatter plot of holding current of autopatched neurons as a function of their depth inside the brain. In FIGS. 11-13, the solid line is the mean, and the dashed lines are mean±standard deviation.

It was found that 20.8% of pipette penetrations (10 out of 48) ended in a successful whole-cell state, defined as that with less than 200 pA of leakage current when held at −65 mV in voltage-clamp mode, which is comparable to the rate reported in literature for fully manual two-photon image-guided patch clamp recordings in vivo [Margrie, T. W. et al. Targeted whole-cell recordings in the mammalian brain in vivo. Neuron 39, 911-918 (2003)]. Even with complete removal of the dura vfrom mouse preparations, some of the pipettes became occluded while moving through the upper cortical layers (FIG. 5B), accounting for several unsuccessful penetrations (n=11 out of 48). If these contaminated pipettes that were automatically retracted by the system before entering the closed-loop pipette positioning stage are not considered, the system has the success rate of 27.0% (10 out of 37).

In an example implementation of the invention, control instructions for the image acquisition and analysis process were implemented using MATLAB. Table 1 contains a list and description of the major control code listings that accompany this disclosure as a Computer Program Listing Appendix, which has been incorporated by reference herein.

TABLE 1

| File Name | Purpose | Notes |
|---|---|---|
| angle_ratio_determination_calibration_HJS.m | Calculates angles and amplitude of micromanipulator movement relative to microscope stage movement | Used during micromanipulator-microscope stage calibration |
| distance_to_travel_diff_calc.m | Calculates optimal trajectory of a patch pipette to a targeted cell | Relies on MATLAB's built-in optimization function (fminsearch) |
| find_cells_gui_SI.m | Builds the GUI; contains functions relevant to each of the stages of two-photon image-guided autopatching; calls image analysis functions | |
| find_center_and_circle_soma_cell_radius_range.m | Analyzes a raw two-photon image to detect boundaries and centroids of cells in the image | Uses user-defined detection criterion to detect cells in the image that meet the criterion |
| find_soma_HJS.m | Calls find_center_and_circle_soma_-cell_radius_range.m | |
| find_one_pipette_HJS.m | Analyzes a z-stack of two-photon images to identify the image in the stack that corresponds to the z-coordinate of the pipette tip and calls a function for identifying x- and y-coordinates from the image | Uses newly developed strategy for tip detection |

TABLE 1-continued

| File Name | Purpose | Notes |
|---|---|---|
| pipette_tip_detection_HJS.m | Analyzes a two-photon image corresponding to the z-coordinate of the pipette tip to determine the x- and y-coordinates of the pipette tip | Uses newly developed strategy for tip detection |
| find_pipette_HJS.m | Calls find_one_pipette_HJS.m | |
| holding_voltage_control_HJS.m | Sends command to the autopatcher control box to apply a desired voltage to the pipette | |
| image_autopatcher_v1.m | Fetches raw two-photon image data from ScanImage and stores the data into variables to be called by other functions; also calls image analysis functions relevant to each of the stages of two-photon image-guided autopatching | |
| load_sensapex_controller_HJS.m | Loads libraries required to interact with micromanipulator controller | |
| move_sensapex_manipulator_HJS.m | Moves the micromanipulator by a specified distance to move the pipette | |
| uman_cleanup_all.m | Clears the libraries loaded by load_sensapex_controller_HJS.m function at the end of the two-photon image-guided autopatcher operation to save memory | |
| plot_scalebar_HJS.m | Plots the scalebar in the GUI throughout the two-photon image-guided autopatching process | |
| pressure_control_HJS.m | Sends command to the autopatcher control box to apply a single desired pressure to the pipette | Uses pressure calibration values determined from using pressure_control_HJS_calibration.m function to find correct command (i.e., voltage) to apply to the valves in the autopatcher control box to produce the desired pressure |
| pressure_control_HJS_calibration.m | Applies a range of voltages to the valves in the autopatcher control box to allow the user to determine what each voltage value translates to in terms of pressure | |
| ramp_pressure_control_HJS.m | Sends command to the autopatcher control box to apply pressure in a ramp of desired slope to the pipette | Uses pressure calibration values determined from using pressure_control_HJS_calibration.m function to find correct command (i.e., voltage) to apply to the valves in the autopatcher control box to produce the desired ramp of pressure |
| ramp_pressure_control_res_meas_HJS.m | Sends command to the autopatcher control box to apply pressure in a ramp of desired slope to the pipette while measuring pipette resistance | Uses pressure calibration values determined from using pressure_control_HJS_calibration.m function to find correct command (i.e., voltage) to apply to the valves in the autopatcher control box to produce the desired ramp of pressure |
| z_stack_acq.m | Calls ScanImage function to acquire a z-stack of two-photon images | Uses user-defined stack properties (i.e., number of images in the stack, step size between consecutive images in the stack) to acquire the z-stack |

A requirement for implementation of the invention was the development of a methodology and apparatus for analyzing the two-photon images acquired using the two-photon laser scanning microscope for detection of the boundaries and centroids of target cells in order to assist in selecting a target cell and acquiring information for automatically guiding the pipette tip to the center of it. The module called find_center_and_circle_soma_cell_radius_range.m was created to analyze a raw two-photon image to detect boundaries and centroids of cells in the image. This module employs a modified version of a previously-reported image analysis technique developed for fluorescent cell detection, but uses user-defined detection criterion, such as cell body radii and cell body brightness, to detect cells in the image that meet the criterion.

Another requirement for implementation of the invention was the development of a methodology and apparatus for using the two-photon images in detection of the location of the pipette tip in order to assist in automatically guiding the tip to the target cell and identifying when contact has been made. The find_one_pipette_HJS.m module uses a newly developed strategy for tip detection and was created to analyze a z-stack of two-photon images in order to identify the image in the stack that corresponds to the z-coordinate of the pipette tip and then call a function for identifying x- and y-coordinates of the pipette tip from the image. A second module, called pipette_tip_detection_HJS.m, also uses the newly developed strategy for tip detection and was created to analyze a two-photon image corresponding to the z-coordinate of the pipette tip to determine the x- and y-coordinates of the pipette tip.

Additionally, new control instructions were developed to improve control of the autopatcher gigaseal formation and break-in processes. The module called pressure_control_HJS.m sends commands to the autopatcher control box to apply a single desired pressure to the pipette. Pressure calibration values determined using the pressure_control_HJS_calibration.m function are used to find the correct command (such as voltage) to apply to the valves in the autopatcher control box in order to produce the desired pressure.

The module called ramp_pressure_control_HJS.m sends commands to the autopatcher control box to apply pressure in a ramp of desired slope to the pipette. The module called ramp_pressure_control_res_meas_HJS.m sends commands to the autopatcher control box to apply pressure in a ramp of desired slope to the pipette while measuring pipette resistance. These modules both employ pressure calibration values determined using the pressure_control_HJS_calibration.m function in order to find the correct command to apply to the valves in the autopatcher control box in order to produce the desired ramp of pressure.

While example implementations of control instructions are presented herein, it will be clear to one of skill in the art that other software platforms, languages, control parameters, and control instructions would also be suitable for use in the control apparatus of the invention and so should be considered to be within the scope of the invention.

Experiments demonstrate that a robotic system according to the invention provides similar recording quality and success rate as fully manual whole-cell recordings in vivo. Since the robot reduces the need for manual manipulation and labor, the system will not only lower the barrier for those new to patch clamp recordings, but also will become a useful tool for expert electrophysiologists. In addition, the modular nature of the methodology will help make the system capable of automated multi-cell patch-clamp recordings, ultimately enabling studies of neuronal networks in the intact brain.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. A method for automated image-guided whole-cell patch clamping, comprising the steps of:
    automated imaging of fluorescently-labeled in vivo cells to produce at least one image of potential target cells;
    identifying and determining the present location of at least one target cell by automated analysis of the at least one potential target cells image;
    open-loop positioning a pipette of an automated cell patch clamping device, the pipette having a tip, by causing the tip of the pipette to be lowered to a predetermined depth in preparation for initiation of target cell contact;
    closed-loop image-guided positioning of the pipette tip to contact the target cell by the steps of:
        determining the initial location of the pipette tip by the steps of:
            taking a stack of images around the location of the pipette tip; and
            automatically detecting the initial location of the pipette tip from the stack of images;
        iteratively lowering the tip of the pipette toward the present location of the target cell by a pre-set amount;
        measuring the resistance at pipette tip after each iteration of the step of lowering;
        identifying whether or not a target cell has been contacted by constructing a temporal series of the resistance measurements after each iteration of the steps of lowering and measuring;
        after each iteration of the steps of lowering, measuring, and identifying target cell contact, imaging the target cell and determining whether or not the location of the target cell has shifted in the x- or y-direction from the previous target cell location;
        if the target cell position has shifted, adjusting the pipette position in the x- and y-direction to account for the target cell position shift; and
        iteratively continuing the steps of lowering, measuring, identifying target cell contact, determining target cell position shift, and adjusting pipette position until the temporal series of resistance measurements indicates monotonic increases in resistance over a threshold number of consecutive iterations and the increase in resistance over the measured temporal series is above a pre-set target cell detection threshold, indicating target cell contact has been achieved;
    stopping the closed-loop image-guided positioning of the pipette after target cell contact has been achieved;
    initiating gigaseal formation;
    assessing whether or not gigaseal formation has been achieved; and
    if gigaseal formation has been achieved, initiating break-in and formation of a whole-cell patch clamp.

2. The method of claim 1, further comprising the step of verifying formation of the whole-cell patch clamp.

3. The method of claim 1, further comprising the step of forming a gigaseal cell-attached patch after gigaseal formation has been achieved.

4. The method of claim 1, the step of adjusting the pipette position in the x- and y-direction further comprising the step of determining x- and y-offsets between the pipette tip and target cell by calculating a current pipette location based on the initial pipette tip location and previous movements of the pipette tip.

5. The method of claim 1, wherein the step of initiating gigaseal formation comprises the step of applying light suction to the cell patch clamping device.

6. The method of claim 5, wherein the step of initiating break-in and patch clamp formation comprises applying strong suction to the cell patch clamping device.

7. The method of claim 1, wherein the step of determining the initial location of the pipette tip comprises identifying the focal plane of the pipette tip by applying filtering and thresholding operations to the images and determining the image in the stack having the brightest pixels most distant from the edge of the image.

8. The method of claim 1, further comprising the step of:
if a predetermined maximum level for lowering the pipette tip has been reached without target cell contact, or gigaseal formation or break-in has not been achieved, retracting the pipette to indicate failure.

9. A method for achieving and verifying target cell contact in an automated image-guided electrophysiology device, comprising the steps of:
automated imaging of fluorescently-labeled in vivo cells to produce at least one image of potential target cells;
identifying and determining the present location of at least one target cell by automated analysis of the at least one potential target cell image;
open-loop positioning a pipette of an automated image-guided electrophysiology device, the pipette having a tip, by causing the tip of the pipette to be lowered to a predetermined depth in preparation for initiation of target cell contact; and
closed-loop image-guided positioning of the pipette tip to contact the target cell by the steps of:
determining an initial location of the pipette tip by the steps of:
taking a stack of images around the location of the pipette tip; and
automatically detecting the initial location of the pipette tip from the stack of images;
iteratively lowering the tip of the pipette toward the present location of the target cell by a pre-set amount;
measuring the resistance at the pipette tip after each iteration of the step of lowering;
identifying whether or not a target cell has been contacted by constructing a temporal series of the resistance measurements after each iteration of the steps of lowering and measuring;
after each iteration of the steps of lowering, measuring, and identifying target contact, imaging the target cell and determining whether or not the location of the target cell has shifted in the x- or y-direction from the previous target cell location;
if the target cell position has shifted, adjusting the pipette position in the x- and y-direction to account for the target cell position shift; and
iteratively continuing the steps of lowering, measuring, identifying target cell contact, determining target cell position shift, and adjusting pipette position until the temporal series of resistance measurements indicates monotonic increases in resistance over a threshold number of consecutive iterations and the increase in resistance over the measured temporal series is above a pre-set target cell detection threshold, indicating target cell contact has been achieved.

10. An apparatus for automated image-guided cell patch clamping, comprising:
a cell patch formation apparatus, comprising:
at least one cell patch clamping device having a recording electrode pipette, the recording electrode pipette having a tip;
a clamping device-positioning 3-axis linear actuator connected to the cell patch clamping device; and
a patch amplifier with computer interface;
a clamping device-moving programmable linear motor connected to the 3-axis linear actuator in a manner permitting moving the cell patch clamping device in a specified direction;
an automated imaging system configured for obtaining images of fluorescently-labeled in vivo cells and of the recording electrode pipette tip;
a resistance monitoring mechanism; and
a computer interface configured for automated closed-loop control of the programmable motor based upon a temporal series of resistance measurements at the tip of the recording electrode pipette and on analysis of pipette and of fluorescently-labeled in vivo cell images acquired from the imaging system.

11. The apparatus of claim 10, further comprising an automated control system configured for:
causing the tip of the recording electrode pipette to be lowered to a predetermined depth for target cell contact;
iteratively causing the tip of the recording electrode pipette to be lowered by a pre-set amount;
measuring the resistance at the recording electrode pipette tip after each iteration of the step of lowering;
determining whether or not a target cell has been contacted by constructing a temporal series of the resistance measurements after each iteration of the steps of lowering and measuring;
after each iteration of the steps of lowering, measuring, and determining target cell contact, imaging the target cell and identifying whether or not the location of the target cell has shifted in the x- or y-direction from the previous target cell location;
if the target cell position has shifted, adjusting the recording electrode pipette position in the x- and y-direction to account for the target cell position shift;
iteratively continuing the steps of lowering, measuring, determining contact, imaging and identifying, and adjusting until the temporal series of resistance measurements indicates monotonic increases in resistance over a threshold number of consecutive iterations and the increase in resistance over the measured temporal series is above a pre-set detection threshold;
stopping the iterative lowering of the recording electrode;
initiating gigaseal formation;
assessing whether or not gigaseal formation has been achieved; and
if gigaseal formation has been achieved, initiating break-in and formation of a whole-cell patch clamp.

12. The apparatus of claim 11, wherein the automated control system is further configured for verifying formation of the whole-cell patch clamp.

13. The apparatus of claim 11, wherein the automated control system is further configured for causing formation of a gigaseal cell-attached patch after gigaseal formation has been achieved and verified.

14. The apparatus of claim 11, wherein the automated control system is further configured for:
measuring the resistance at the recording electrode tip;
assessing whether or not the measured resistance has increased over a pre-set tip blockage threshold; and
if the measured resistance has increased over the tip blockage threshold, directing the linear motor to retract the cell patch clamping device to indicate tip blockage and failure.

15. The apparatus of claim 10, further comprising a controllable plurality of pneumatic valves configured for application of pressure and suction to the cell patch clamping device.

16. The apparatus of claim 15, wherein the controllable plurality of pneumatic valves and the automated control system are further configured for applying light suction to the cell patch clamping device during initiation of gigaseal formation.

17. The apparatus of claim 15, wherein the controllable plurality of pneumatic valves and the automated control system are further configured to apply strong suction to the cell patch clamping device to initiate break-in and whole-cell patch clamp formation.

18. The apparatus of claim 10, wherein the automated imaging system comprises a two-photon laser scanning microscope.

19. A method for controlling an automated image-guided cell patch clamping device, comprising the steps of:
in an apparatus for automated cell patch clamping, comprising:
a cell patch formation apparatus, comprising:
at least one cell patch clamping device having a recording electrode pipette, the recording electrode pipette having a tip;
a clamping device-positioning 3-axis linear actuator connected to the cell patch clamping device; and
a patch amplifier with computer interface;
a clamping device-moving programmable linear motor connected to the 3-axis linear actuator in a manner permitting moving the cell patch clamping device in a specified direction;
an automated imaging system configured for obtaining images of fluorescently-labeled in vivo cells and of the recording electrode pipette tip;
a resistance monitoring mechanism; and
a computer interface configured for automated closed-loop control of the programmable motor based upon a temporal series of resistance measurements at the tip of the recording electrode pipette and on analysis of pipette and of fluorescently-labeled in vivo cell images acquired from the imaging system;
performing the steps of:
automated imaging of fluorescently-labeled in vivo cells to produce at least one image of potential target cells;
identifying and determining the present location of at least one target cell by automated analysis of the at least one potential target cells image;
open-loop positioning of a pipette of an automated cell patch clamping device, the pipette having a tip, by causing the tip of the pipette to be lowered to a predetermined depth in preparation for initiation of target cell contact;
closed-loop image-guided positioning of the pipette tip to contact the target cell by the steps of:
determining the initial location of the pipette tip by the steps of:
taking a stack of images around the location of the pipette tip; and
automatically detecting the initial location of the pipette tip from the stack of images;
iteratively lowering the tip of the pipette toward the present location of the target cell by a pre-set amount;
measuring the resistance at pipette tip after each iteration of the step of lowering;
identifying whether or not a target cell has been contacted by constructing a temporal series of the resistance measurements after each iteration of the steps of lowering and measuring;
after each iteration of the steps of lowering, measuring, and identifying target cell contact, imaging the target cell and determining whether or not the location of the target cell has shifted in the x- or y-direction from the previous target cell location;
if the target cell position has shifted, adjusting the pipette position in the x- and y-direction to account for the target cell position shift; and
iteratively continuing the steps of lowering, measuring, identifying target cell contact, determining target cell position shift, and adjusting pipette position until the temporal series of resistance measurements indicates monotonic increases in resistance over a threshold number of consecutive iterations and the increase in resistance over the measured temporal series is above a pre-set target cell detection threshold, indicating target cell contact has been achieved;
stopping the closed-loop image-guided positioning of the pipette after target cell contact has been achieved;
initiating gigaseal formation;
assessing whether or not gigaseal formation has been achieved; and
if gigaseal formation has been achieved, initiating break-in and formation of a whole-cell patch clamp.

20. The method of claim 19, wherein the cell patch formation apparatus further comprises a controllable plurality of pneumatic valves configured for application of pressure and suction to the cell patch clamping device and wherein the step of initiating gigaseal formation further comprises applying light suction to the cell patch clamping device and the step of initiating break-in and formation comprises applying strong suction to the cell patch clamping device.

* * * * *